Figure 1:
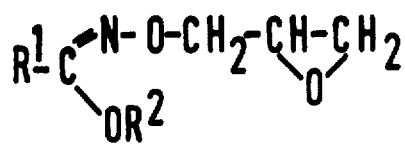

United States Patent [19]

Gebert et al.

[11] 4,150,043

[45] Apr. 17, 1979

[54] O-(2,3-EPOXYPROPYL)-HYDROXIMIC ACID ESTERS

[75] Inventors: Ulrich Gebert, Kelkheim; Werner Thorwart, Wiesbaden, both of Fed. Rep. of Germany

[73] Assignee: Hoechst Aktiengesellschaft, Frankfurt, Fed. Rep. of Germany

[21] Appl. No.: 849,935

[22] Filed: Nov. 9, 1977

[30] Foreign Application Priority Data

Nov. 9, 1976 [DE] Fed. Rep. of Germany ....... 2651085

[51] Int. Cl.$^2$ .......................................... C07D 303/16
[52] U.S. Cl. ................................................ 260/348.44
[58] Field of Search ................................... 260/348.44

*Primary Examiner*—Norma S. Milestone

*Attorney, Agent, or Firm*—Littlepage, Quaintance, Murphy, Richardson and Webner

[57] ABSTRACT

Compounds of general formula

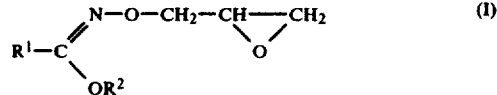

wherein $R^1$ represents a radical selected from the group consisting of an alkyl group having from 1 to 6 carbon atoms, an unsubstituted aryl group having 6 carbon atoms, an aryl group having 6 carbon atoms being substituted by at least one radical selected from the group consisting of a chlorine atom, alkyl and alkoxy each having up to 2 carbon atoms; and $R^2$ represents an alkyl group having from 1 to 6 carbon atoms.

4 Claims, 8 Drawing Figures

O-(2,3-EPOXYPROPYL)-HYDROXIMIC ACID ESTERS

This invention relates to novel O-(2,3-epoxypropyl)-hydroximic acid esters and processes for their preparation.

According to one aspect of the present invention there are provided compounds of general formula

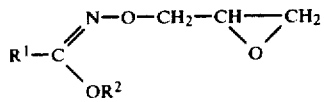 (I)

wherein $R^1$ represents a straight-chained or branched alkyl group having from 1 to 6 carbon atoms, or an aryl group having up to 6 carbon atoms optionally substituted by one or more chlorine atoms or alkyl or alkoxy groups having up to 2 carbon atoms; and $R^2$ represents an alkyl group having from 1 to 6 carbon atoms.

The compounds according to the present invention are valuable intermediates for the synthesis of 3-substituted O-(2-hydroxypropyl)-hydroxylamines which have interesting biological and pharmacological properties.

In compounds of general formula I in which the aryl radical is substituted, the aryl group generally has from 1 to 3 identical or different substituents selected from alkyl and alkoxy groups having up to 2 carbon atoms and chlorine atoms. The groups $R^1$ and $R^2$ in the compounds according to he invention may be the same or different, for example, methyl, ethyl, propyl, isopropyl, n-butyl, isobutyl, tert.-butyl, and the various pentyl and hexyl groups. When $R^1$ represents an aryl group, these groups may be, for example phenyl, tolyl or chlorophenyl groups. $R^1$ and $R^2$ are, however, preferably alkyl groups with 1 to 4 carbon atoms and $R^1$ is also preferably an aromatic hydrocarbon radical.

Especially useful compounds according to the invention are:
ethyl O-(2,3-epoxypropyl)-acetohydroximate; and
methyl O-(2,3-epoxypropyl)-benzohydroximate.

It is not possible to prepare the compounds of general formula I directly from hydroxylamine per se, as it is known that selective O-alkylation of hydroxylamine is only successful when the more nucleophilic amino group is blocked. This may be effectively achieved by forming the hydroximic acid esters of formula

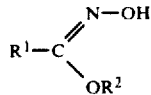 (II)

(in which $R^1$ and $R^2$ are as hereinbefore defined),

Thus, according to a further aspect of the invention there are provided processes for the preparation of compounds of general formula I, which comprise reacting a compound of formula II or an alkali metal salt thereof, with (a) an alkylating agent of formula

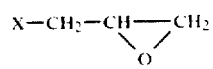 (III)

(in which X represents a chlorine or bromine atom or a sulphonic acid ester group);

(b) an alkylating agent in the form of a 2-propanol of formula

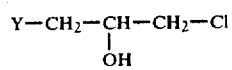 (IV)

(in which Y represents a bromine atom or a sulphonic acid ester group) under formation of HY and subsequently dehydrohalogenating the chlorohydrins thereby formed in the presence of a base; or (c) an alkylating agent of the formula $$X-CH_2-CH=CH_2 \quad (V)$$

(in which X is as hereinbefore defined) and the olefin thereby formed is epoxidized.

Reaction of the hydroximic acid esters of formula II with the alkylating agents of formulae III to V is preferably effected in an anhydrous medium. Appropriate solvents are, for example, alcohols such as methanol, ethanol or propanol, and preferably solvents which are inert under the reaction conditions, e.g. ethers such as dioxan, tetrahydrofuran, diethyl ether, diisopropyl ether or diethylene glycol dimethyl ether; hydrocarbons such as hexane, petroleum ether, benzene, toluene or xylene; halogenated and/or nitrated hydrocarbons such as dichloromethane, chloroform, carbon tetrachloride, ethyl chloride or chlorobenzene and/or nitrobenzene; esters such as ethyl acetate; aprotic solvents such as dimethylformamide, dimethylacetamide or dimethyl sulphoxide; or, if desired, an excess of the alkylating agents themselves.

It is particularly preferred to effect the alkylation with the hydroximic acid esters of formula II in the form of their alkali metal salts. The alkylation is conveniently effected at a temperature of from 0° C. to the boiling point of the solvent. Reaction times are generally from 1 to 5 hours.

Process (a) according to the invention is preferably effected using a compound of formula II in the form of an alkali metal salt thereof which is reacted with epichlorohydrin.

Dehydrochlorination of chlorohydrins produced in process (b) is advantageously carried out in a solvent which is inert under the reaction conditions such as, for example, the above-mentioned ethers or hydrocarbons, in the presence of a base, such as, for example, alkali metal or alkaline-earth metal hydroxides or carbonates, preferably potassium, sodium or calcium hydroxide or potassium or sodium carbonate, conveniently at temperatures of from 0° C. to 150° C., preferably, however, from 20° to 100° C., and generally within 0.5 to 8 hours.

Epoxidation of the olefin compounds produced in process (c) can be carried out, for example, with peroxy acids, such as, for example, perbenzoic acid, 3-chloroperbenzoic acid, monoperphthalic acid, monopersuccinic acid, peracetic acid or pertungstenic acid, and preferably in solvents which are inert under the reaction conditions, such as the above-mentioned solvents, especially chloroform, ethyl acetate, ethyl chloride, ethers such as diethyl ether, tetrachloromethane or dimethylformamide. The reaction is conveniently effected at a temperature of from −10° to +40° C., and preferably at ambient temperature. It has proved especially advantageous to allow the reaction mixture of the olefin and peroxy acid, which is preferably used in a small excess, to stand at room temperature for up to 24 hours.

Preparation of alkali metal salts of the compounds of formula II used as starting materials in the processes according to the invention may be carried out, for example, using stoichiometric quantities of alkali metal hydroxides, carbonates, metals, hydrides, amides, lower alkali metal alcoholates (in which the alkyl radical has 1 to 4 carbon atoms, e.g. lithium, sodium or potassium methylate, ethylate or tert.butylate) or organometallic compounds, such as butyl lithium, phenyl lithium or phenyl sodium, in the solvents conventionally used therefor, preferably in hydrocarbons, at temperatures between 0° and 30° C. It has proved particularly favourable to use sodium methylate in methanolic solution with an equivalent quantity at room temperature of the appropriate hydroximic acid ester of formula II which is stirred briefly for approximately 10 to 60 minutes. Subsequent removal of the solvent by distillation gives the dry, easily powdered, stable sodium hydroximates which, for example, in process (a), are advantageously suspended in epichlorohydrin in a molar ratio of 1:(2–5), whereby a vigorous exothermic reaction takes place which may be optionally effected with careful heating. To effect completion of this reaction process, the mixture may, if desired, be heated for up to 3 or more hours at 105° to 115° C. Precipitated sodium chloride may be easily removed by shaking out with water after the addition of excess ether. The pure liquid final products of formula I may be isolated advantageously by fractional distillation under reduced pressure.

The surprisingly stable O-(2,3-epoxypropyl)-hydroxylamine derivatives of general formula I may be obtained in a facile reaction by these single stage processes and as mentioned above these compounds are good starting substances for the synthesis of novel polyfunctional O-alkylhydroxylamines having interesting pharmacological properties such as, for example, the compounds described in our copending patent application No. 850,057 (corresponding to German Patent Application No. P 26 51 083.8) of the same date, namely, Nov. 9, 1977.

Many hydroxylamine derivatives, some having valuable biological properties, are known. Thus, for example, the preparation has been reported of some O-(2-hydroxyalkyl)-hydroxylamines, without further functional groups in the alkyl radical, by the N-hydroxyurethane method of E. Testa et al. [Helv. Chim. Acta 45, 358,1381 (1962)] and the N-hydroxyphthalimide method of W. Kliegel [Pharmazie 25, 400, 525 (1970)].

According to one aspect of the present invention there are provided compounds of general formula

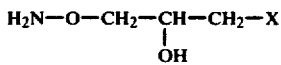

wherein X represents a group of the formula

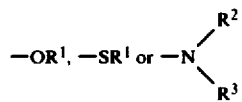

in which $R^1$ represents
(a) a hydrogen atom,
(b) an amino group, when X represents an —OR$^1$ moiety,
(c) an alkyl group having from 1 to 6 carbon atoms or
(d) a mono- or binuclear aryl group optionally substituted by one or more halogen atoms or alkyl, alkoxy, halogenoalkyl groups each having up to 4 carbon atoms, cycloalkyl groups having 3 to 6 carbon atoms, nitro or cyano groups; and $R^2$ and $R^3$, which may be the same or different, each represents
(a) a hydrogen atom,
(b) an alkyl group having from 1 to 6 carbon atoms or cycloalkyl group having from 3 to 7 carbon atoms and optionally substituted by one or more hydroxy groups or alkoxycarbonyl groups having 1 to 4 carbon atoms,
(c) an aralkyl or diaralkyl group having 1 to 4 carbon atoms in the alkyl moiety and being optionally substituted in the alkyl moiety by hydroxy groups, and optionally substituted in the aryl moieties by one or more alkoxy groups having from 1 to 4 carbon atoms or halogen atoms,
(d) a mono- or binuclear aryl group optionally substituted by one or more alkyl, alkoxy or halogenoalkyl groups each having up to 4 carbon atoms or halogen atoms,
(e) a hydroxy group when the other of $R^2$ and $R^3$ is hydrogen, or
(f) $R^2$ and $R^3$, together with the nitrogen atom to which they are attached, represent a 5- to 7-membered saturated ring optionally substituted by an alkyl group having from 1 to 4 carbon atoms, and the ring being optionally interrupted by an oxygen, sulphur or further nitrogen atom or,
(g) $R^2$ and $R^3$, together with the nitrogen atom to which they are attached, represents a 5-membered heteroaromatic ring containing up to 4 nitrogen atoms and being optionally formed with a benzene- or uracil-ring and physiologically acceptable acid addition salts thereof.

Preferred compounds by reason of their favorable pharmacological properties are:

O-(3-phenoxy-2-hydroxypropyl)-hydroxylamine;
O-[3-(p-chlorophenoxy)-2-hydroxypropyl]-hydroxylamine;
O-[3-(2,4-dichlorophenoxy)-2-hydroxypropyl]-hydroxylamine;
O-[3-(3-methylphenoxy)-2-hydroxypropyl]-hydroxylamine;
O-[3-(4-methoxyphenoxy)-2-hydroxypropyl]-hydroxylamine;
O[3-(4-cyanophenoxy)-2-hydroxypropyl]-hydroxylamine;
O[3-(3-trifluoromethylanilino)-2-hydroxypropyl]-hydroxylamine;
O-[3-(4-diphenylmethyl-piperzin-1-yl)-2-hydroxypropyl]-hydroxylamine and physiologically acceptable acid addition salts thereof.

In the Drawings

Figure 2:
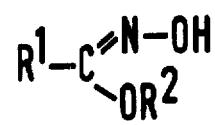
Figure 3:
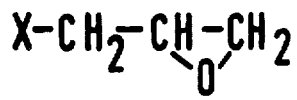

FIG. 1 is Formula (I).
FIG. 2 is Formula (II).
FIG. 3 is Formula (III).

Figure 4:
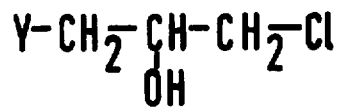
Figure 5:
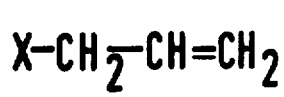
Figure 6:
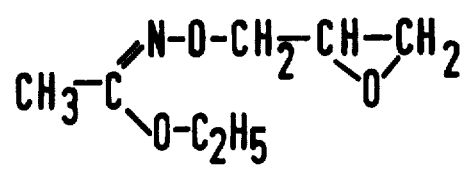
Figure 7:
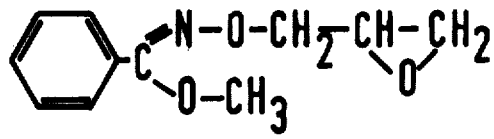
Figure 8:
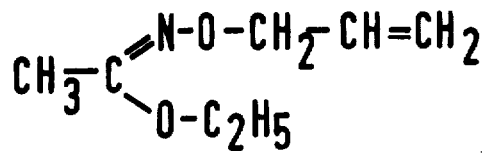

FIG. 4 is Formula (IV).
FIG. 5 is Formula (V).
FIG. 6 is Formula (VI).
FIG. 7 is Formula (VII).
FIG. 8 is Formula (VIII).

There is provided the following process for the preparation of compounds of general formula

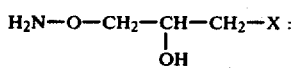

reacting an O-alkylated hydroxylamine derivative of formula

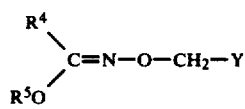

with a compound of formula

HR⁶ to form a common intermediate compound of formula

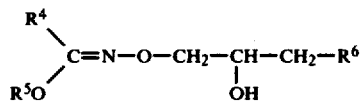

and subsequently removing the protecting group of formula

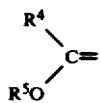

to form a compound of formula

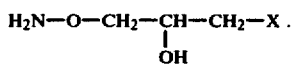

In the above formulae:

R⁴ represents a straight-chained or branched alkyl group having from 1 to 6 carbon atoms or a mono- or binuclear aryl group optionally substituted by one or more alkyl or alkoxy groups having up to 2 carbon atoms or halogen atoms;

R⁵ represents a straight-chained or branched alkyl group having from 1 to 6 carbon atoms;

R⁶ is as hereinbefore defined for X or represents a group of the formula

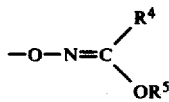

(in which R⁴ and R⁵ are as hereinbefore defined);

Y represents a group of the formula

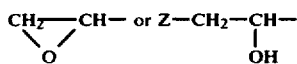

(in which

Z represents a halogen, preferably chlorine or bromine atom, or a reactive sulphonic acid ester group).

Example for preparation of O-[3-(3,4-Dichlorophenoxy)-2-hydroxypropyl]hydroxylamine hydrochloride A solution of 16.3 g (0.1 mol) of 3,4-dichlorophenol and 10.1 g (0.1 mol) of triethylamine in 100 ml of dimethylformamide is mixed with 15.9 g (0.1 mol) of ethyl O-(2,3-epoxypropyl)acetohydroximate and the reaction mixture is stirred for 40 hours at 95°–100° C. Afterwards, the solvent is distilled off under reduced pressure and the residue fractionally distilled under reduced pressure to give 26.2 g (81.3% of theory) of ethyl O-[3-(3,4-dichlorophenoxy)-2-hydroxypropyl]-acetohydroximate of boiling point (3 mm Hg) 178°–180° C. To give the hydroxylamine, the distillate (81.3 mmol) is heated in 100 ml of 2N hydrochloric acid for 15 minutes with reflux, the cooled solution is evaporated to dryness under reduced pressure and the solid residue is recrystallised from ethanol.

Yield: 16.4 g (70% of theory); melting point 152° C. (with decomposition). $C_9H_{12}Cl_3NO_3$ (M.W.=288.6)

Analysis: Calculated C 37.46%; H 4.19%; Cl 36.86%; N 4.85%. Found C 37.43%; H 4.29%; Cl 36.42%; N 4.83%.

The following Examples serve to illustrate the preparation of compounds of general formula I. In these Examples the structure of the compounds produced has been determined by their elemental analysis, and i.r. and ¹H-n.m.r. spectra.

EXAMPLE 1

Ethyl O-(2,3-Epoxypropyl)-acetohydroximate of formula

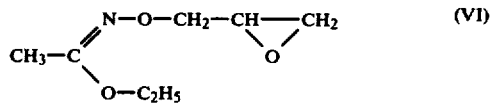

A. By alkylation with epichlorohydrin

To a freshly prepared solution of 11.5 g (0.5 gram atom) of metallic sodium in 300 ml of anhydrous methanol are added, at room temperature, 51.5 g (0.5 mol) of ethyl acetohydroximate. The mixture is stirred for 30 minutes and the alcohol is distilled off under reduced pressure and with the exclusion of moisture. After drying at a high temperature in a high vacuum the sodium salt residue is suspended in 200 ml (2.5 mol) of freshly distilled epichlorohydrin and slowly heated with vigorous stirring. At approximately 60° C. a vigorous exothermic reaction starts, and the temperature of the mixture rises spontaneously to over 90° C. with the precipitation of sodium chloride. The mixture is maintained for 2 hours at 100° to 110° C., left to cool to room temperature, mixed with 500 ml diethyl ether and the sodium chloride removed by shaking twice with 300 ml portions of water. The organic phase is separated and dried over sodium sulphate, the ether is evaporated off in vacuo at room temperature and the liquid residue is fractionally distilled under reduced pressure.

Yield: 55 g (69.1% of theory); boiling point (11 mm Hg) 82°–84° C.

$C_7H_{13}NO_3$ (m.w.=159.2):

Analysis: Calculated: C 52.8%; H 8.25%; N 8.8%. Found: C 52.7%; H 8.5%; N 8.7%.

B. By alkylation with 2,3-epoxypropyl-p-toluene sulphonate

To a suspension of 6.0 g of 80% sodium hydride (0.2 mol) in 200 ml of dimethylformamide are added with stirring 20.6 g (0.2 mol) of ethyl acetohydroximate and the mixture is stirred for 30 minutes at room temperature to give a clear solution. The mixture is heated to 50° C. and at this temperature 45.7 g (0.2 mol) of 2,3-epoxypropyl-p-toluene sulphonate in 20 ml of dimethylformamide are added dropwise. The mixture is subsequently heated with continuous stirring for 1 hour to 80° C., after cooling the solvent is removed under reduced pressure, the residue mixed with 50 ml of water and the product extracted with diethyl ether. After drying the ether phase over sodium sulphate, the solvent is evaporated off and the oily residue is fractionally distilled under reduced pressure.

Yield: 18.4 g (57.8% of theory); boiling point (15 mm Hg) 85°–87° C.

If the alkylation reaction of the sodium salt of ethyl acetohydroximate is carried out with 2,3-epoxypropyl-p-toluene sulphonate in ethanol as solvent, a yield of only 40% is obtained.

EXAMPLE 2

Methyl O-(2,3-epoxypropyl)-benzohydroximate of formula

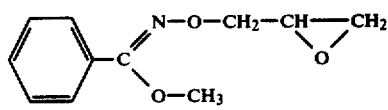
(VII)

Analogously to Example 1, 30.2 g (0.2 mol) of methyl benzohydroximate are converted with sodium methylate to the corresponding sodium salt which is subsequently reacted with 78 ml (1 mol) of epichlorohydrin. After heating for 3 hours under reflux the mixture is allowed to cool, 200 ml of water are added and the reaction product is shaken with 500 ml of diethyl ether. The ether phase is dried over sodium sulphate, the solvent removed by distillation and the oily residue is fractionally distilled under reduced pressure.

Yield: 15.9 g (38.4% of theory); boiling point (0.4 mm Hg) 135° to 137° C.

$C_{11}H_{13}NO_3$ (m.w = 207.3);

Analysis: Calculated: C 63.76%; H 6.32%; N 6.76%. Found: C 63.65%; H 6.43%; N 6.98%.

EXAMPLE 3

Ethyl O-(2,3-epoxypropyl)-acetohydroximate of formula

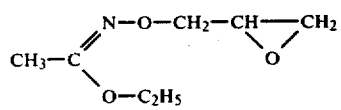
(VI)

1st stage: Ethyl O-allyl-acetohydroximate of formula

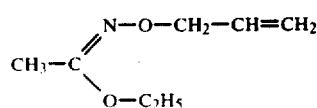
(VIII)

To a sodium methylate solution prepared from 11.5 g (0.5 gram atom) of sodium in 200 ml of anhydrous methanol are added 51.5 g (0.5 mol) of ethyl acetohydroximate. The resulting clear reaction mixture is heated to 50° C. and then 60.5 g (0.5 mol) of allyl bromide are added dropwise. The mixture is subsequently heated for 1 hour under reflux, then cooled, filtered from sodium bromide precipitated, and the solvent is distilled off under reduced pressure. The residue obtained is dissolved in 300 ml of diethyl ether. After washing several times with water, drying the organic phase over sodium sulphate and evaporation of the ether, an oil is obtained which is fractionally distilled under reduced pressure.

Yield: 51 g (71.2% of theory); boiling point (32 mm Hg)

66°–67° C.; $a_D{}^{25} = 1.4290$.

$C_7H_{13}NO_2$ (m.w = 143.2)

2nd stage: Ethyl O-(2,3-epoxypropyl)-acetohydroximate

A solution of 45 g (0.21 mol) of 80% 3-chloroperbenzoic acid in 250 ml of chloroform is mixed with 26.1 g (0.18 mol) of ethyl O-allyl-acetohydroximate. The mixture is then stirred for 24 hours at room temperature. It is then filtered from 3-chlorobenzoic acid precipitated, washed with chloroform and residual acid is removed from the organic phase by repeatedly shaking with 10% sodium hydroxide solution. After washing neutral with water, the mixture is dried over sodium sulphate, the solvent evaporated off under reduced pressure and the oily residue is fractionally distilled.

Yield: 5.7 g (20% of theory), boiling point (15 mm Hg) 84°–86° C.

$C_7H_{13}NO_3$ (159.2)

of formula VI

Analysis: Calculated: C 52.8%; H 8.25%; N 8.8%. Found: C 52.9%; H 8.40%; N 8.6%.

It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

What we claim is:

1. Compounds of general formula

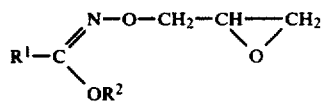
(I)

wherein $R^1$ represents a radical selected from the group consisting of an alkyl group having from 1 to 6 carbon atoms and an unsubstituted aryl group having 6 carbon atoms and $R^2$ represents an alkyl group having from 1 to 6 atoms.

2. Compounds of general formula I as claimed in claim 1 wherein $R^1$ represents a radical selected from the group consisting of methyl and phenyl and $R^2$ is an alkyl having up to 2 carbon atoms.

3. Ethyl O-(2,3-epoxypropyl)-acetohydroximate.

4. Methyl O-(2,3-epoxypropyl)-benzohydroximate.